US011219547B2

(12) United States Patent
Schertiger et al.

(10) Patent No.: US 11,219,547 B2
(45) Date of Patent: Jan. 11, 2022

(54) OSTOMY APPLIANCE

(71) Applicant: Coloplast A/S, Humlebaek (DK)

(72) Inventors: Lars Olav Schertiger, Fredensborg (DK); Lars Gudmand Pedersen, Hilleroed (DK)

(73) Assignee: Coloplast A/S, Humlebaek (DK)

( * ) Notice: Subject to any disclaimer, the term of this patent is extended or adjusted under 35 U.S.C. 154(b) by 822 days.

(21) Appl. No.: 15/769,742

(22) PCT Filed: Oct. 19, 2016

(86) PCT No.: PCT/DK2016/050334
§ 371 (c)(1),
(2) Date: Apr. 20, 2018

(87) PCT Pub. No.: WO2017/067557
PCT Pub. Date: Apr. 27, 2017

(65) Prior Publication Data
US 2020/0246173 A1    Aug. 6, 2020

(30) Foreign Application Priority Data

Oct. 20, 2015  (DK) .......................... PA 2015 70680
Oct. 20, 2015  (DK) .......................... PA 2015 70682
May 20, 2016  (DK) .......................... PA 2016 70340

(51) Int. Cl.
*A61F 5/448*  (2006.01)
*A61F 5/445*  (2006.01)
*A61F 5/443*  (2006.01)

(52) U.S. Cl.
CPC .............. *A61F 5/448* (2013.01); *A61F 5/443* (2013.01); *A61F 5/445* (2013.01)

(58) Field of Classification Search
CPC ........... A61F 5/448; A61F 5/445; A61F 5/443
See application file for complete search history.

(56) References Cited

U.S. PATENT DOCUMENTS 3,713,445  A      1/1973  Marsan
4,923,452  A *   5/1990  Hunger .................. A61F 5/448
                                                                  604/338

(Continued)

FOREIGN PATENT DOCUMENTS

EP       1872751 A2    1/2008
EP       2315561 A2    5/2011

(Continued)

*Primary Examiner* — Ariana Zimbouski
(74) *Attorney, Agent, or Firm* — Coloplast Corp., Coloplast A/S; Nick Baumann (57) ABSTRACT

An ostomy appliance (20) including a sealing wafer (22) with a first adhesive (32) having a first opening (34) configured to be attached to a skin surface around an ostomy of a user, and a bag (36) for collecting stomal output that includes a second adhesive (44) configured to engage with the skin surface radially outside of the sealing wafer. The sealing wafer and the bag are configured to be connectible to each other either in direct connection or by a coupling interface. One kind of coupling interface includes one or more pipe sections (50). The ostomy appliance allows for differentiation of adhesive types for different purposes, such as sealing and load carrying.

28 Claims, 7 Drawing Sheets

(56) References Cited

U.S. PATENT DOCUMENTS

| | | | |
|---|---|---|---|
| 5,000,748 A * | 3/1991 | Fenton | A61F 5/443 604/340 |
| 5,147,340 A * | 9/1992 | Lavender | A61F 5/448 604/344 |
| 5,160,330 A | 11/1992 | Cross | |
| 5,167,651 A | 12/1992 | Leise, Jr. et al. | |
| 5,269,773 A | 12/1993 | Vidal | |
| 5,865,819 A | 2/1999 | Cisko, Jr. et al. | |
| 5,961,502 A | 10/1999 | Amery | |
| 6,312,415 B1 | 11/2001 | Nielsen et al. | |
| 7,722,586 B2 | 5/2010 | Mullejans et al. | |
| 8,319,003 B2 | 11/2012 | Olsen et al. | |
| 8,652,112 B2 | 2/2014 | Johannison et al. | |
| 8,679,082 B2 | 3/2014 | Bach et al. | |
| 8,684,982 B2 | 4/2014 | Nguyen-Demary et al. | |
| 2005/0054997 A1 | 3/2005 | Buglino et al. | |
| 2005/0261646 A1 * | 11/2005 | Conrad | A61F 5/449 604/338 |
| 2007/0156105 A1 | 7/2007 | Blum | |
| 2008/0154220 A1 * | 6/2008 | Gaffney | A61F 5/445 604/333 |
| 2010/0241092 A1 | 9/2010 | Nguyen-Demary et al. | |

FOREIGN PATENT DOCUMENTS

| | | |
|---|---|---|
| GB | 2290974 A1 | 1/1996 |
| GB | 2408211 A | 5/2005 |
| RU | 128102 U1 | 5/2013 |
| WO | 9834573 A1 | 8/1998 |
| WO | 03026541 A1 | 4/2003 |
| WO | 2009023870 A1 | 2/2009 |
| WO | 2010006600 A2 | 1/2010 |
| WO | 14177723 A1 | 11/2014 |

\* cited by examiner

OSTOMY APPLIANCE

SUMMARY

Aspects of the present disclose provide an ostomy appliance in accordance with the appended claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following, an axial direction is defined as the direction of the stoma, when the appliance is worn by a user. Thus, the axial direction is substantially perpendicular to a skin surface of a user, such as an abdominal skin surface. A radial direction is defined as transverse to the axial direction.

Whenever referring to the proximal side of a device or part of a device, the referral is to the skin-facing side, when the ostomy appliance is worn by a user. Whenever referring to the distal side of a device or part of a device, the referral is to the side facing away from the skin, at least when the ostomy appliance is worn by a user. Put differently, the proximal side is the side closest to the user, when the appliance is fitted on a user and the distal side is the opposite side—the side furthest away from the user in use.

It is to be understood that the features of the various exemplary embodiments described herein may be combined with each other, unless specifically noted otherwise. Nothing in the description of the different figures shall be taken to mean that a discussed feature is necessarily only applicable to the exact illustration plotted in a related figure, unless obviously recognizable to the opposite effect or specifically noted otherwise.

In the following, the words 'ostomy' and 'stoma' and any related or derived wordings thereof are used interchangeably without any intention to have different meanings.

Embodiments provide an ostomy appliance including a sealing wafer with a first adhesive having a first opening configured to be attached to a skin surface around an ostomy of a user, and a bag for collecting stomal output that includes a second adhesive configured to engage with the skin surface radially outside of the sealing wafer in relation to an axis extending through a first centre of a sealing wafer opening and a second centre of a collecting bag inlet opening.

Embodiments provide an ostomy appliance wherein the portion of adhesive material subject to stress from carrying the weight of the stomal output collected in the bag is separate from the portion of adhesive material subject to the aggressive stomal output fluids. According to the disclosure, the adhesive material subjected to carrying a vast majority of the weight of the collecting bag is the second adhesive, whereas the adhesive material subjected to the stomal output is the first adhesive on the sealing wafer. One advantage of the disclosure is the provision of an ostomy appliance structure that allows for a much higher degree of substantial differentiation between types of adhesive material. According to the disclosure, the adhesive material of the first adhesive can be tailored to withstand the aggressive substances of the stomal output. Similarly, the adhesive material of the second adhesive can be tailored to provide a suitably strong adhesive connection to the skin surface for carrying the weight of the collecting bag, practically without any concern of disintegration of the adhesive matrix by stomal fluids. Thereby, the effects of the individual components of the different adhesives can be enhanced and exploited to a higher degree than with known adhesive systems for ostomy appliances, resulting in an appliance having little or no need for balanced and compromised properties of the adhesive matrix. Consequently, both the first adhesive providing sealing capabilities to the appliance and the second adhesive providing load carrying capabilities to the appliance can be optimized to more distinctively each solve their individual target problem.

Embodiments provide an ostomy appliance allowing for an increase in wear-time of the wafer, which leads to fewer changes of the adhesive wafer carrying the weight of the collecting bag and thus to less skin irritation caused by attaching and detaching adhesive material from the skin surface.

Figure 1:
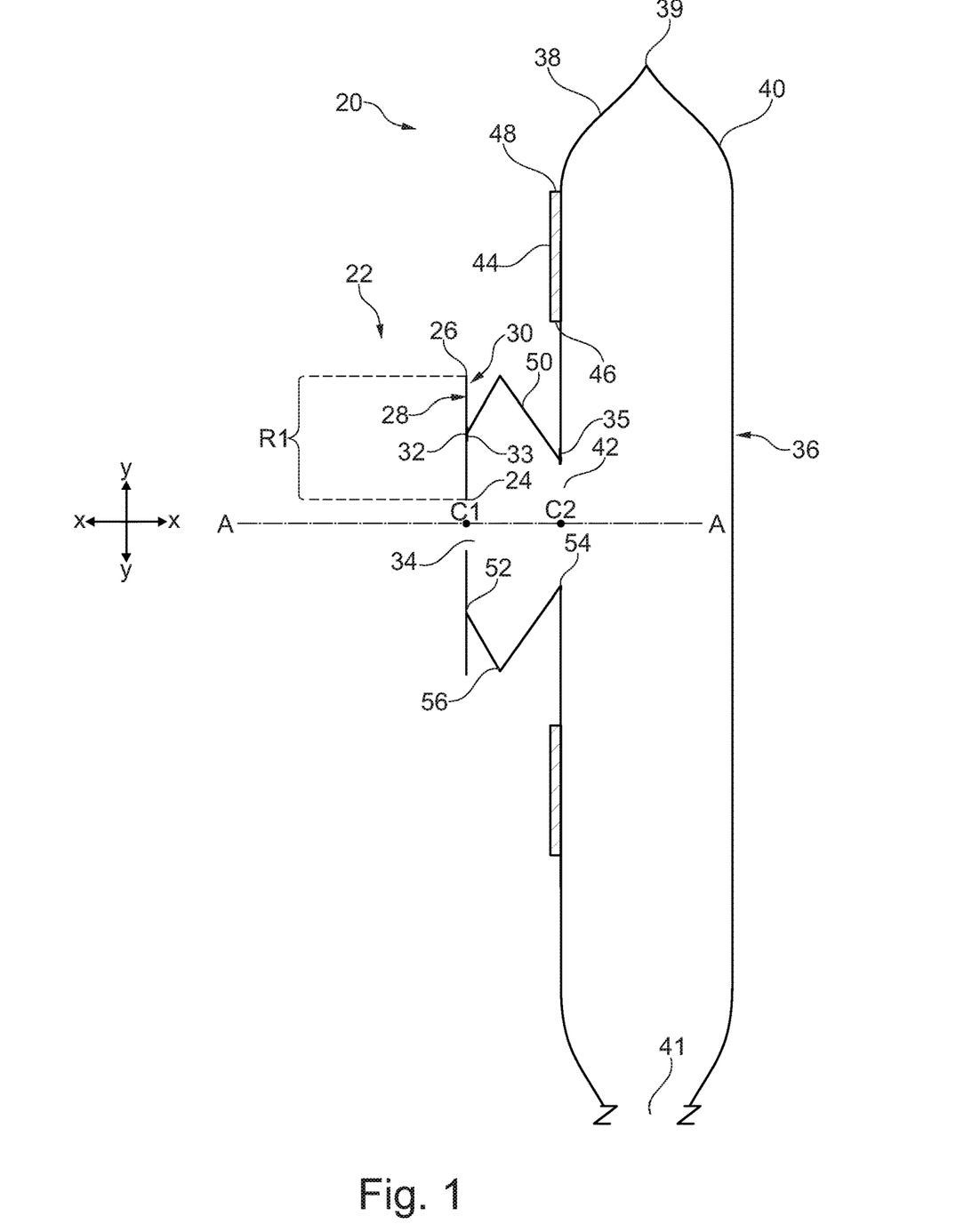
FIG. 1 is a cross-sectional side view of one embodiment of an ostomy appliance.

FIG. 1 is a schematic cross-sectional side view of one embodiment of an ostomy appliance 20 including a sealing wafer 22 and a stomal output collecting bag 36 ('collecting bag 36'). The sealing wafer 22 has a first radial extent R1 between a first inner periphery 24 and a first outer periphery 26 of the sealing wafer 22. The sealing wafer 22 defines a first proximal surface 28 provided with a first adhesive 32 and an at least partly exposed second distal surface 30. The first adhesive 32 is adapted for engagement to a skin surface of a user and therefore presents skin-friendly characteristics.

In one embodiment, the first adhesive 32 is an adhesive including polyisobutylene, styrene-isoprene-styrene and hydrocolloids such as, but not limited to, the types of adhesives disclosed in WO 99/11302. The sealing wafer 22 further defines a stoma-receiving opening 34 at the first inner periphery 24. In one embodiment, the sealing wafer 22 is adapted to allow the stoma-receiving opening 34 to be customized to a size and shape of a user's individual stoma. In embodiments, the sealing wafer 22 comprises an elastic top film or a backing film 86 (FIG. 7) that is able to conform together with the adhesive material 32 of the sealing wafer 22 to any adapted shape of the stoma-receiving opening 34.

The collecting bag 36 includes a proximal wall 38 and a distal wall 40. The walls 38, 40 are joined along at least a portion of their outer periphery 39 to form a collecting volume inside the collecting bag 36. In some embodiments, the collecting bag 36 includes a foldable outlet (not shown) at a lower portion 41 of the collecting bag 36 for intermittent emptying of accumulated stomal output from the collecting bag 36. The collecting bag 36 includes an inlet opening 42 in the proximal wall 38 of the bag 36 for receiving the output.

The sealing wafer 22 and the collecting bag 36 are adapted to be connectible to each other.

In one embodiment, the sealing wafer 22 and the collecting bag 36 are fixedly connected to each other. 'Fixedly' means that the sealing wafer 22 and the collecting bag 36 cannot be separated from each other without breaking the connection and rendering the appliance useless. However, it does not mean that the sealing wafer 22 and the proximal wall 38 of the collecting bag 36 are completely immovable, or locked in position, in relation to each other.

In another embodiment, the sealing wafer 22 and the collecting bag 36 are detachably connected to each other. 'Detachably' means that the sealing wafer 22 and the collecting bag 36 can be connected and separated from each other without breaking the connection and the sealing wafer 22 of the appliance 20 can thus continue to function, e.g. if the collecting bag 36 is exchanged for a new one.

The ostomy appliance 20 further includes a second adhesive 44 provided on the proximal wall 38 of the collecting bag 36 around the inlet opening 42. In one embodiment, the second adhesive 44 is defined between a second inner periphery 46 and a second outer periphery 48. In embodiments, the second adhesive can be an adhesive of the types described in the publications WO 99/11302 or WO 2009/006901.

At least in use, i.e. in a situation where a user has attached the ostomy appliance 20 to the skin surface around a stoma, the first outer periphery 26 of the sealing wafer 22 is adapted to be located radially closer to an axis A-A extending through a first centre C1 of the stoma-receiving opening 34 and a second centre C2 of the inlet opening 42 than any portion of the second adhesive 44 on the proximal wall 38. In other words, any individual point on an exposed surface of the second adhesive 44 is located at a second radial distance from the axis A-A that is greater than a first radial distance between the axis A-A and the first outer periphery 26 of the sealing wafer 22. In one embodiment, the second adhesive 44 is configured to be located annularly around the first adhesive 32 of the sealing wafer 22.

The ostomy appliance 20 according to the present disclosure provides a solution wherein the load from the weight of the collecting bag itself and of the accumulated stomal output is carried almost exclusively by the second adhesive 44 on the proximal wall 38 of the collecting bag 36. By 'almost exclusively' is to be understood that any contribution to the load-carrying or load-bearing capability of the ostomy appliance 20 from the first adhesive 32 is negligible compared to the second adhesive 44. In other words, the first adhesive 32 on the proximal surface 28 of the sealing wafer 22, which is adapted to be located on and around a peristomal skin surface, is not required to have load bearing capabilities or characteristics. Instead, the first adhesive 32 can be optimized towards creating an improved and efficient seal having greater resistance against deterioration caused by stomal output attacking the integrity of the adhesive material. This is advantageous in that it allows for a structure of an ostomy appliance 20 that provides for easier attachment to the skin (the user has access to the at least partly disposed second distal surface 30 of the sealing wafer 22 during application of the appliance to the skin) and also for increased security against disintegration of the adhesive matrix, which in turn means less skin complications (caused by stomal output) and reduced risk of loss of adhesion (appliance slipping off skin because of breaking-down of adhesive and adhesion). Suitable types of adhesives for the first adhesive 32 include, but are not limited to, paste-like adhesives of the types disclosed in WO 2010/069334. In embodiments, more than one type of adhesive material is used for the first adhesive 32. In such embodiments, the different adhesive materials can be provided in a side-by-side configuration and/or in a layered configuration.

FIG. 1 further illustrates one embodiment, wherein the sealing wafer 22 and the collecting bag 36 are fixedly connected to each other. In FIG. 1, the sealing wafer 22 and the proximal wall 38 of the collecting bag 36 are fixedly, but floatingly, attached to each other. By 'floatingly' attached is to be understood that the sealing wafer 22 is attached to the collecting bag 36 such that movement of the sealing wafer 22 in a direction Y (up/down in relation to the proximal wall 38, see FIG. 1) and/or in a direction X (away from/closer to the proximal wall 38, see FIG. 1) does not necessarily cause an immediate, relative movement of the proximal wall 38 of the collecting bag 36. The 'floating' attachment between the sealing wafer 22 and the proximal wall 38 further helps provide for the first adhesive 32 to be free from any load bearing of the weight of the bag 36 when it is attached to the skin surface of a user, and also helps to prevent any direct pulling or shear forces caused by external force applied to the collecting bag 36 from being translated to the first adhesive 32 of the sealing wafer 22.

Figure 3:
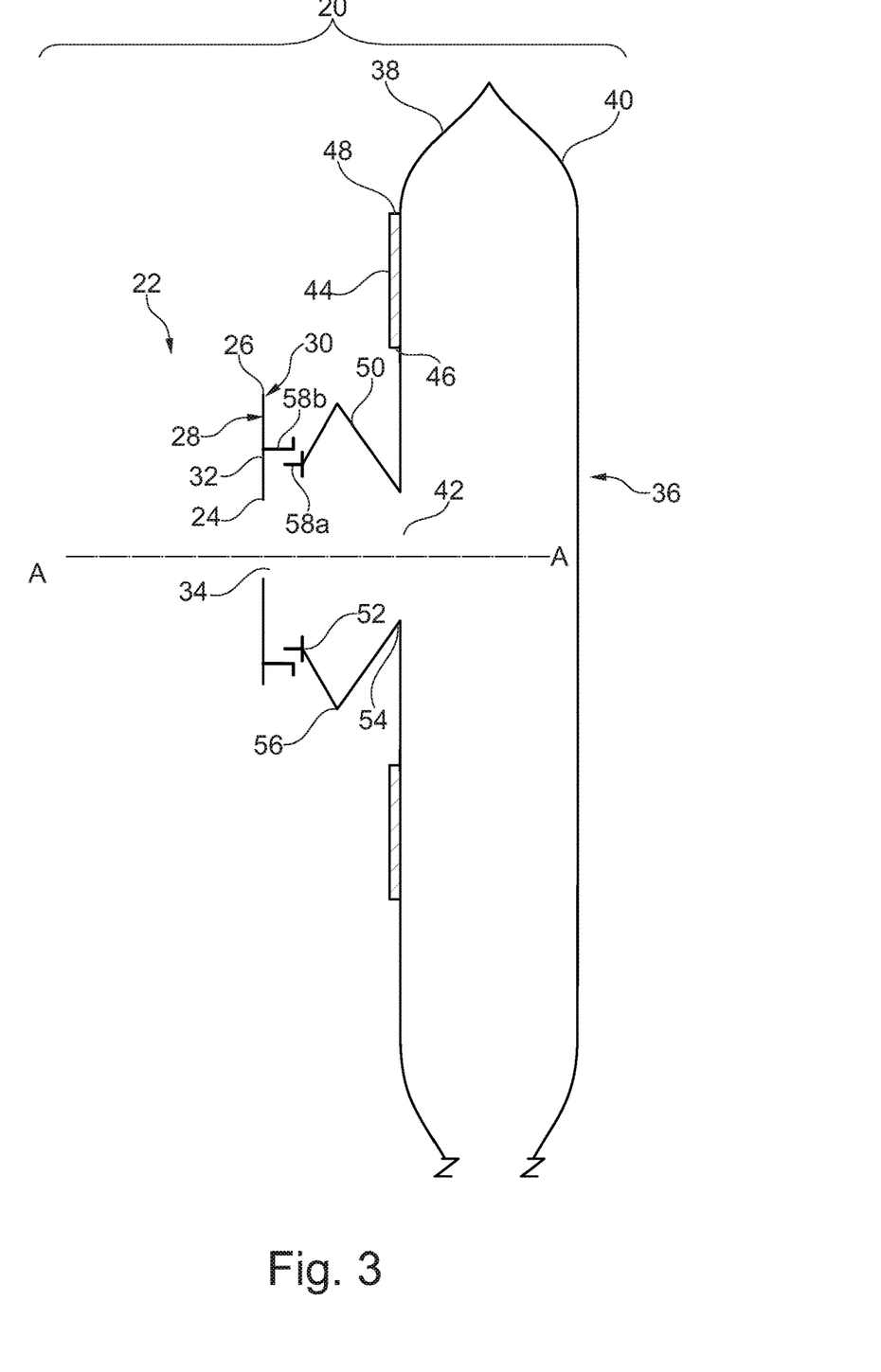
FIG. 3 is a cross-sectional side view of one embodiment of an ostomy appliance.

In one embodiment, the sealing wafer 22 is fixedly and floatingly attached to the proximal wall 38 by a plastic tube 50. In one embodiment, a first end 52 of the plastic tube 50 is attached to the second distal surface 30 of the sealing wafer 22 and a second end 54 of the plastic tube 50 is attached to the proximal wall 38 of the collecting bag 36 (FIG. 3). In one embodiment, the plastic tube 50 has a straight configuration without any folds or bends. In embodiments, the plastic tube 50 provides a safe and flexible connection between the sealing wafer 22 and the collecting bag 36.

In embodiments, the plastic tube 50 is attached to the sealing wafer 22 at a first weld zone 33 and to the proximal wall 38 at a second weld zone 35. In embodiments, the plastic tube 50 is adapted with an axial extent to allow for an axial displacement of a first plane extending through (containing) the second distal surface 30 away from a second plane extending through (containing) the proximal wall 38 of the collecting bag 36 along the axis A-A. In embodiments, the plastic tube 50 is configured to allow for such axial displacement in the range of 10-70 mm In one embodiment, the plastic tube 50 includes one or more applications 56 allowing the plastic tube 50 to be extended (stretched) such that the sealing wafer 22 is movable relative to the proximal wall 38 of the collecting bag 36. In one embodiment, a plurality of applications 56 that combine to form an accordion-like structure of the plastic tube 50 between the second distal surface of the sealing wafer 22 and the proximal wall 38 of the collecting bag 36. In this disclosure, a 'plurality' should be understood as two or more. In addition to the safety and flexibility of the plastic tube 50, the accordion-like application(s) 56 of the plastic tube 50 provides for the plastic tube 50 to be extended (stretched) and thereby for the sealing wafer 22 to be movable in the directions of the arrows X and Y indicated in FIG. 1. This is additionally advantageous in that it allows a user to apply a relatively substantial distance between the sealing wafer 22 and the collecting bag 36 during application of the appliance 20 to the skin to improve the quality or certainty of correct mounting. This is further particularly advantageous in situations where a user's stoma is located in a hard to reach or hard to see area of the skin surface.

In embodiments, the sealing wafer 22 is fixedly and floatingly attached to the proximal wall 38 of the collecting bag 36 by a thermoplastic sheet material adapted to form an enclosed passage or canal, provided that the thermoplastic sheet material ensures a liquid and odor tight connection with the proximal wall 38 of the collecting bag 36, for safe direction of the stomal output from the stoma and into the collecting bag 36.

Figure 2:
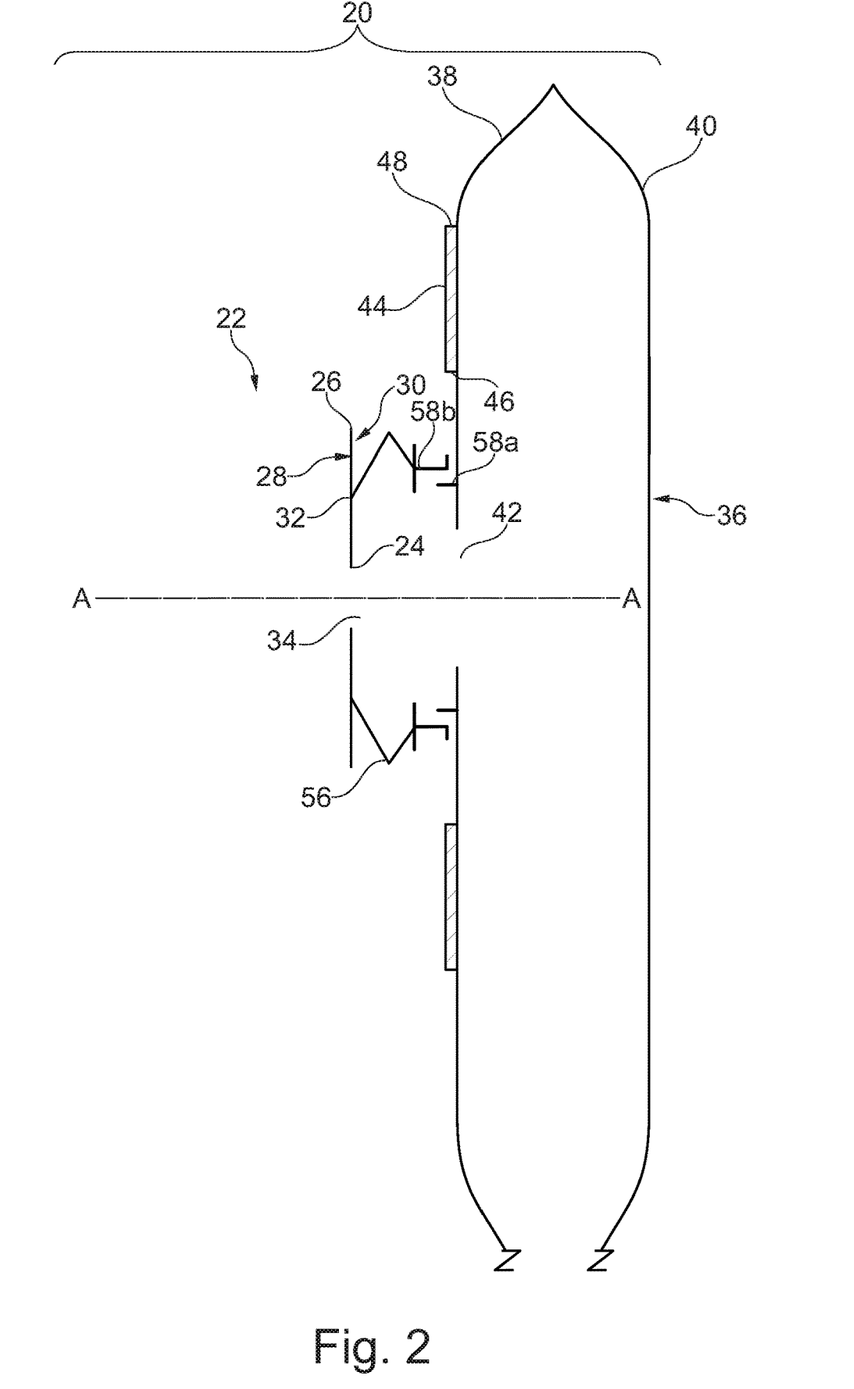
FIG. 2 is a cross-sectional side view of one embodiment of an ostomy appliance.

FIGS. 2 and 3 are schematic cross-sectional side views of embodiments of an ostomy appliance 20, wherein the sealing wafer 22 and the collecting bag 36 are detachably connected to each other.

In one embodiment, a first half of a coupling interface is provided on the proximal wall 38 of the collecting bag 36 and a second half of the coupling interface is connected to the second distal surface of the adhesive wafer 22 with a plastic tube 50. In another embodiment, the first half of the coupling interface is provided on the second distal surface of the adhesive wafer 22 and the second half of the coupling interface is connected to the proximal wall 38 of the collecting bag 36 with a plastic tube 50.

In the embodiment shown in FIG. 2, a first half 58a of a coupling interface is provided on the proximal wall 38 of the collecting bag 36 and a second half 58b of the coupling interface is connected to the second distal surface 30 of the sealing wafer 22 with a plastic tube 50.

In the embodiment shown in FIG. 3, a first half 58a of a coupling interface is provided at a first end 52 of a plastic tube 50. A second end 54 of the plastic tube 50 is connected to the proximal wall 38 of the collecting bag 36. A second half 58b of the coupling interface is provided on the second distal surface 30 of the sealing wafer 22. In embodiments, the plastic tube 50 is made from a flexible, polyethylene film, but other flexible film materials are acceptable. In embodiments, the plastic tube 50 is made from the same material as the proximal and distal walls 38, 40 of the collecting bag 36. In embodiments, one suitable material for the walls 38, 40 of the collecting bag 36 is a barrier film, such as, but not limited to, SealedAir® barrier films available from Dow Chemicals. In one embodiment, the plastic tube 50 is formed as a continuation or extension of the proximal wall 38 towards and into connection with the sealing wafer 22, either to form a fixed connection or a coupled connection.

In embodiments, the second half 58b of the coupling interface is connected to the second distal surface 30 of the sealing wafer 22 by a plastic tube 50.

In embodiments, the first half 58a of the coupling interface and the second half 58b of the coupling interface are welded or glued to the proximal wall 38 and the second distal surface 30, respectively, and/or to the first end 52 and to the second end 54 of the plastic tube 50. In embodiments, the first and second halves 58a, 58b of the coupling interface can include first and second mechanical coupling halves, first and second engaging flanges where at least one flange has an adhesive provided on it, first and second magnetic coupling parts, first and second hook-and-loop type coupling parts to give some examples. In some implementations, the plastic tube 50 is adapted to form a sleeve or sleeve-like element connecting the sealing wafer 22 and the collecting bag 36. The sleeve forms an enclosed passage through which stomal output is led into the collecting bag 36.

Figure 4:
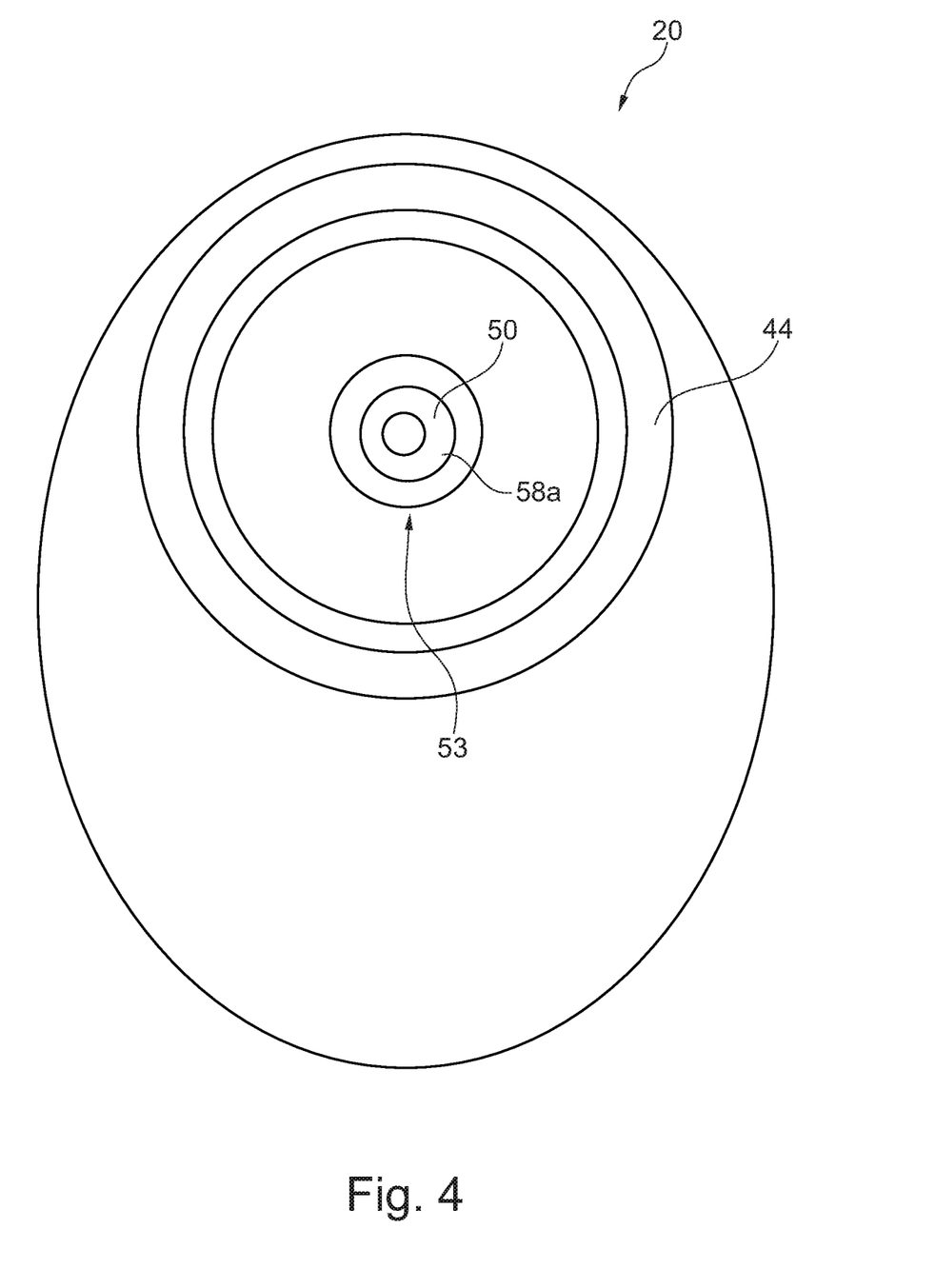
FIG. 4 is a plan view of a proximal side of one embodiment of an ostomy appliance.
Figure 5:
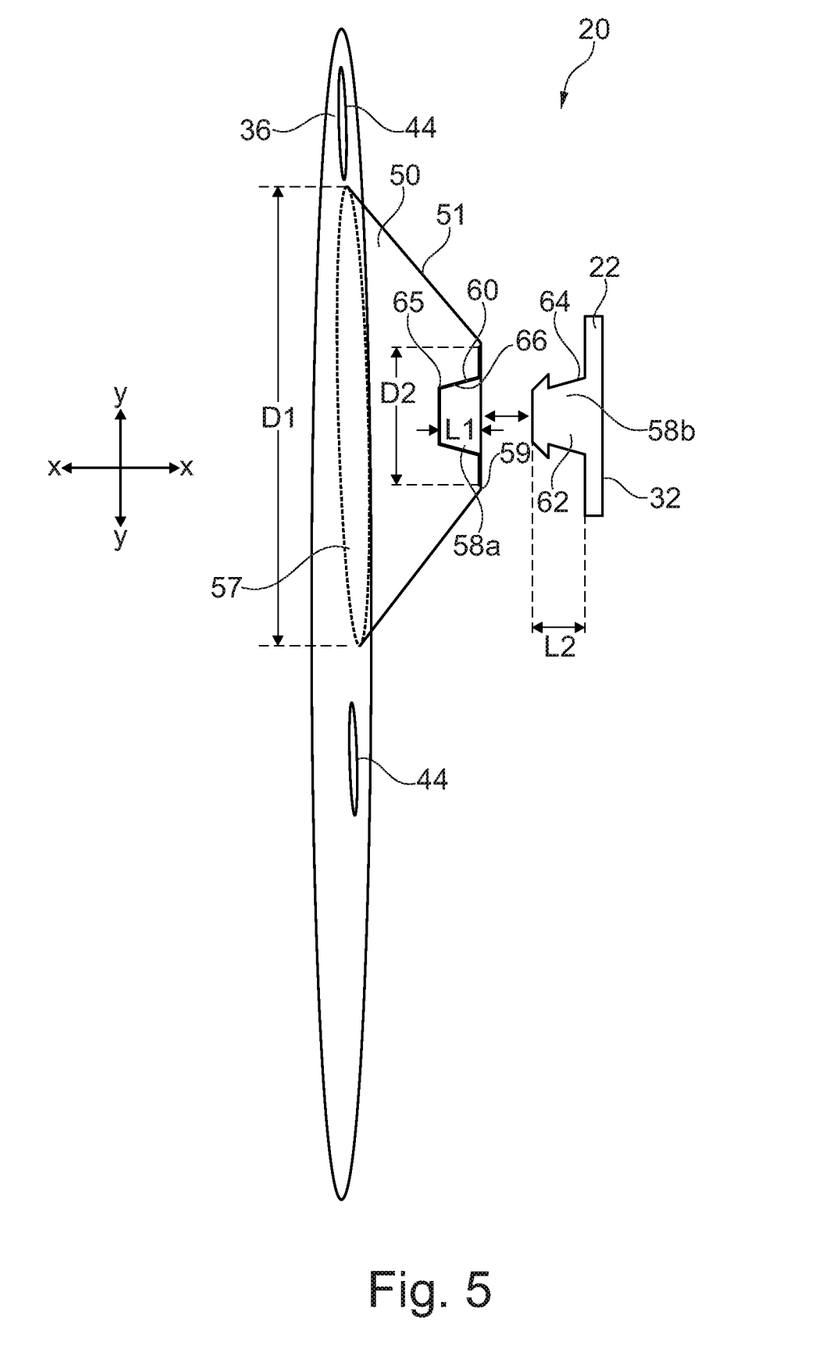
FIG. 5 is a schematic, part cross-sectional side view of one embodiment of an ostomy appliance.

In one embodiment, the plastic tube 50 is configured with a conical shape such that the plastic tube 50 has a first, relatively larger diameter D1 at the plastic tube's 50 connection 57 to the proximal wall 38 of the collecting bag 36 than a second, relatively smaller diameter D2 at the plastic tube's 50 connection 59 to the first half 58a of the coupling interface. One exemplary implementation of this embodiment is illustrated in the view of FIGS. 4 and 5. In FIG. 5, a wall 51 of the plastic tube 50 is shown in an extended (stretched) situation. However, it is to be understood that the plastic tube 50 provides the coupling interface with some flexibility (in terms on manoeuvring options) in that the first coupling half 58a on the collecting bag end can move in the directions of the arrows X and Y. This is advantageous also in that any body movements of the user, subjecting the ostomy appliance to stress and strain (e.g. by the appliance being influenced or impacted by body shapes, skin folds, clothing, belts etc.), will be "absorbed" by the flexibility of the coupling interface provided generally by the plastic tube 50. In turn, this is believed to increase the wear comfort of the appliance for the user. In one embodiment, the wall 51 of the plastic tube 50 includes a transparent film material. Thereby, the user is able to ascertain that the coupling halves 58a, 58b are properly and correctly engaged before applying the second adhesive 44 to the skin after application of the sealing wafer 22.

FIG. 4 is a plan view of the proximal side of one embodiment of an ostomy appliance wherein a comfort element 53 is provided to surround the plastic tube 50, the comfort element 53 including a soft stretch fabric material, textile material or non-woven material. In embodiments, the comfort element 53 is attached to the collecting bag 36 around the connection 57 and to the first half 58a of the coupling interface around the connection 59. The comfort element 53 is advantageously provided to further increase the wear comfort of the ostomy appliance 20 in that the skin of the user will not be directly exposed to the material of the plastic tube 50.

Referring now to embodiments of the presented disclosure, presented by way of example by the illustration in FIG. 5, at least one of the first half 58a of the coupling interface and the second half 58b of the coupling interface is formed as a relatively rigid pipe section 60, 62. In one embodiment, as illustrated in FIG. 5, the first half 58a of the coupling interface includes a first pipe section 60 and the second half 58b of the coupling interface includes a second pipe section 62. By 'relatively rigid' is to be understood that the material(s) and/or the structure of the pipe section(s) 60, 62 provides the pipe section(s) with some stiffness and resiliency, such that the pipe section(s) allows for some, but not permanent, deformation, when the first half 58a of the coupling interface and the second half 58b of the coupling interface are brought into engagement. In embodiments, the pipe section(s) 60, 62 comprise(s) a tubular or conical inner lumen defined by an annular wall portion of significantly greater rigidity than the material of the plastic tube 50. In some embodiments, the pipe section(s) 60, 62 are configured to return to initial or original shape after having been coupled. It is noted that, although the embodiment of FIG. 5 illustrates that the second pipe section 62 is centred on the sealing wafer 22, this is not a requirement. In embodiments, the second pipe section 62 is displaced in a radial direction in relation to a centre of the sealing wafer 22. Among other advantages, this provides for an increased versatility of the ostomy appliance 20 in terms of options of locating the appliance on the user's skin, particularly for users having a stoma location that is problematic.

In one embodiment, the outer surface 64 of the second pipe section 62 is provided with, or formed as, a conical shape, which provides for reducing the friction between the pipe sections 60, 62 during coupling and further acts to provide a guided coupling action for the user. In one embodiment, the inner surface 66 of the first pipe section 60 is provided with a conical shape adapted to receive the outer surface 64 of the section pipe section 62. Particularly, but not exclusively, embodiments wherein both the outer surface 64 of the second pipe section 62 and the inner surface 66 of the first pipe section 60 are formed with a conical shape provide for a guided coupling action aiding the user in correctly bringing the halves of the coupling interface into engagement.

Figure 6:
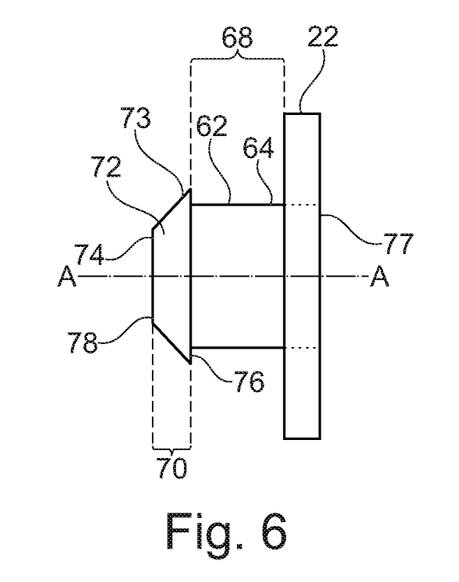
FIG. 6 is a schematic side view of one embodiment of an ostomy appliance.

In an embodiment, as illustrated in the view of FIG. 6, all points on an outer surface 64 of a major portion 68 of the second pipe section 62 are located with an equal distance to a centre axis A-A through the second pipe section 62, such that the major portion 68 of the outer surface 64 forms the shape of a cylinder. In embodiments (not illustrated), all points on an inner surface 66 of the first pipe section 60 are located with an equal distance to a centre axis A-A through the first pipe section 60, such that the inner surface 66 of the first pipe section 60 forms the shape of a cylinder. Put differently, the major portion 68 of the outer surface 64 and/or the inner surface 66 can be said to have a straight (linear) shape when viewed in cross-section.

In some embodiments, an outer surface 64 of the second pipe section 62 and/or an inner surface 66 of the first pipe section 60 includes a surface treatment, such as a coating with a slip agent or similar substance, providing for reducing the friction between the pipe sections 60, 62 during coupling.

With further reference to the illustrated embodiments of FIG. 6, in embodiments, the second pipe section 62 includes an end portion 70 including a collar 72. The collar 72 defines an opening 74 of the second pipe section 62. In embodiments, the collar 72 includes a ledge or neck portion 76. In embodiments, the collar 72 includes a tapering external surface 73 extending from the neck portion 76 to a first periphery 78 of the collar 72 at the opening 74. In embodiments, the neck portion 76 extends radially beyond the outer surface 64 of the major portion 68 of the second pipe section 62. The tapering external surface 73 of the collar 72 assists both in reducing the friction between the second pipe section 62 and the first pipe section 60, and in guiding the user towards correct coupling.

In embodiments, a length L2 (FIG. 5) of the second pipe section 62 parallel to the axis A-A is generally in the range of 15-40 mm. As stomas are very different in size and length (in terms of "how much" intestine protrudes from the skin surface), the 15-40 mm range mentioned is considered to be an adequate interval to meet the needs of most users. However, because of the individuality, even longer or even shorter second pipe sections 62 may be relevant and are considered to be part of the present disclosure.

In embodiments, the collar 72 of the second pipe section 62 is made from a flexible material, thereby providing one option of configuring the collar 72 so that it can pass through the first pipe section 60. In alternative embodiments, the collar 72 includes one or more hollow portions or recesses thereby providing flexibility. In embodiments, the second pipe section 62 is made from a different material than the material of the first pipe section 60. In embodiments, the material of the second pipe section 62 is stiffer or more rigid than the material of the first pipe section 60.

In embodiments, a length L1 (FIG. 5) of the first pipe section 60 parallel to the axis A-A is generally shorter than the length L2 of the second pipe section 62. In embodiments, L1 is generally approximately 3-7 mm, such as 5 mm, shorter than L2. Such configurations of the lengths L1 and L2 provide for a robust and tight coupling between the first and second halves 58a, 58b of the coupling interface.

In embodiments, the ledge or neck portion 76 is configured to provide a stop adapted to abut against a second periphery 65 of the first pipe section 60 in the coupled configuration of the ostomy appliance 20. This helps provide for a robust and tight coupling between the first and second halves 58a, 58b of the coupling interface. Thereby, the ostomy appliance 20 has a reduced risk of unintentional decoupling or separation of the coupling interface, in turn providing a greater security against leakage incidents, a phenomenon recognized as being of primary concern to ostomists. Moreover, some ostomists experience a pressure build-up in the collecting bag 36 caused by spikes in the production of flatus gases and/or by the collecting bag volume being temporarily reduced (e.g. due to the user's movements) or permanently reduced (e.g. because of stomal output accumulating in the bag). In embodiments including the stop of the ledge or neck portion 76 abutting the second periphery 65, an additional advantage is achieved in that any such pressure build-up generating a pressure force acting on the first and second pipe sections 60, 62, provides for the neck portion 76 of the second pipe section 62 to more firmly abut the second periphery 65 of the first pipe section 60. Thereby, it helps provide more security against unintentional decoupling of the coupling interface as well as reducing the likelihood of leakage incidents.

In some embodiments, the coupling interface is configured to give off a signal in response to correct coupling of the coupling interface. In embodiments, the signal is a sound signal. In embodiments, the sound signal is generated mechanically. In embodiments, the mechanical generation of the sound signal defines a 'snap' or 'click' sound when the neck portion 76 of the second pipe section 62 is brought into abutment with the second periphery 65 of the first pipe section 60.

In some embodiments of the ostomy appliance 20, particularly, but not exclusively, embodiments including first and/or second pipe sections 60, 62, the sealing wafer 22 with the first adhesive 32 can be configured to have a relatively small adhesive area (surface 28) compared to the adhesive area of traditional ostomy appliances. This is at least partly due to the separation of the functions of the adhesive between the first adhesive 32 (sealing, leakage prevention) and the second adhesive 44 (load carrying, stabilizing of the ostomy appliance). Not only can the first adhesive 32 thereby be tailored to its sealing purpose, the area of the first adhesive 32 can also be smaller in size. This is advantageous both in terms of material (and ultimately product) costs and in terms of reducing the size of the peristomal skin surface subject to the influence of an adhesive, which is beneficial to the skin condition. In embodiments, an outer diameter of the sealing wafer 22 ranges between Ø 50-60 mm.

In embodiments, the opening 74 (FIG. 6) is configured to define an exit for the user's stoma (not shown). In embodiments, the user's stoma enters the second pipe section 62 at the opposite end opening 77 and extends through the second pipe section 62 to exit at opening 74.

Figure 7:
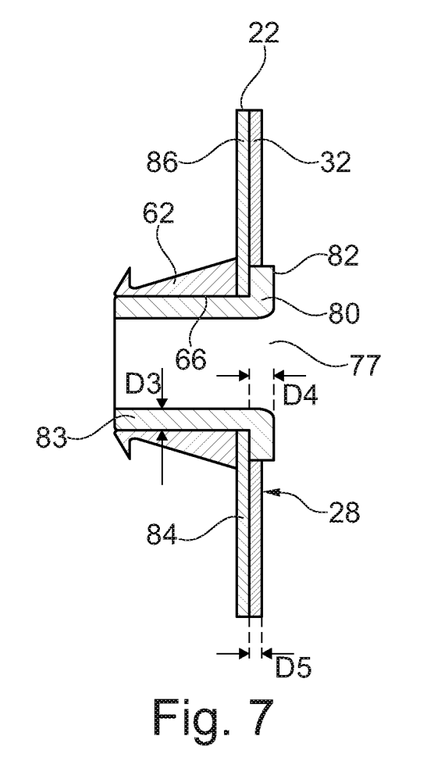
FIG. 7 is a cross-sectional view of one embodiment of an ostomy appliance.

FIG. 7 illustrates a cross-sectional view of an embodiment, wherein the second pipe section 62 includes a lining 80 inserted in the lumen defined by the second pipe section 62 to cover or clothe the inner surface 66 of the second pipe section 62. In embodiments, the lining 80 includes a non-permeable formable material having a memory. Suitable materials include, but are not limited to, polyurethane based foams. 'Memory' means that the material causes the lining 80 to re-expand after having been compressed. In embodiments, the lining 80 has a wall 83 having a thickness D3 of approximately 1-2 mm. In embodiments, the lining 80 comprises a ridge 82 defined at the opening 77 and configured to be supported on the proximal surface 28 of the sealing wafer 22. In embodiments, the ridge 82 is supported on a radially innermost portion of the proximal surface 28. In embodiments, the ridge 82 is supported on the proximal surface 28 annularly around and adjacent to the opening 77. In embodiments, the ridge 82 is adapted to be attached to a proximal side of the backing film 86 with a glue or adhesive 84. In embodiments, the glue or adhesive 84 is provided at a lower surface of the ridge 82 adjacent to the wall 83 of the lining 80. Thereby, the lining 80 can be connected to the second pipe section 62 before, and controlled during, application of the ostomy appliance 20. Among other advantages, the lining 80 helps provide good sealing effect between the user's stoma (not shown) and the second pipe section 62. In embodiments, the formable material of the lining 80 is adapted to be in direct contact with the outer surface of the stoma, thereby further increasing sealing capability. In other embodiments, the lining 80 is adapted to define an inner diameter that does not directly contact the outer surface of the stoma.

With further reference to FIG. 7, in embodiments, the sealing wafer 22 includes backing film 86 and a first adhesive 32. In embodiments, the ridge 82 is configured to have an extent D4, measured parallel to the wall 83 of the lining 80, of between 0.1-2.0 mm more than a thickness D5 of the first adhesive 32. This is advantageous in further helping to provide good sealing effects between the stoma and the first adhesive 32 of the sealing wafer 22.

In embodiments, the ostomy appliance 20 further comprises a plug or stopper configured to have an outer diameter adapted to match a diameter of the opening 74 in the collar 72, alternatively match or be slightly larger than an inner diameter of the lumen defined by the lining 80 when inserted into the second pipe section 62. This provides the user with an option to temporarily seal off the flow of stomal output from the stoma during the time it takes to exchange the collecting bag 36 in embodiments where the ostomy appliance 20 is provided as a 2-piece system having a coupling interface.

In an alternative embodiment, the sealing wafer 22 includes a backing film 86 made from a relatively thicker silicone material and a first adhesive 32 provided as an adhesive paste material. In embodiments, the paste material of the first adhesive 32 is provided as an initially separate adhesive ring adapted to be adhered to the silicone material of the sealing wafer 22. This advantageously provides embodiments, wherein the sealing wafer 22, including the silicone material and the second pipe section 62, is provided as a re-useable unit. When the ostomy appliance 20 is due to be exchanged, the re-useable unit can be taken off the skin, rinsed and cleaned to be free from stomal output and residual adhesive, and subsequently a new adhesive ring can be connected to the silicone material of the re-useable unit and then applied to the skin together with a new collecting bag 36. This is advantageous at least in that a new second pipe section 62 and a new backing film 86 are not required at each exchange of appliance. Suitable silicone materials are disclosed in WO 03/026541.

Figure 8:
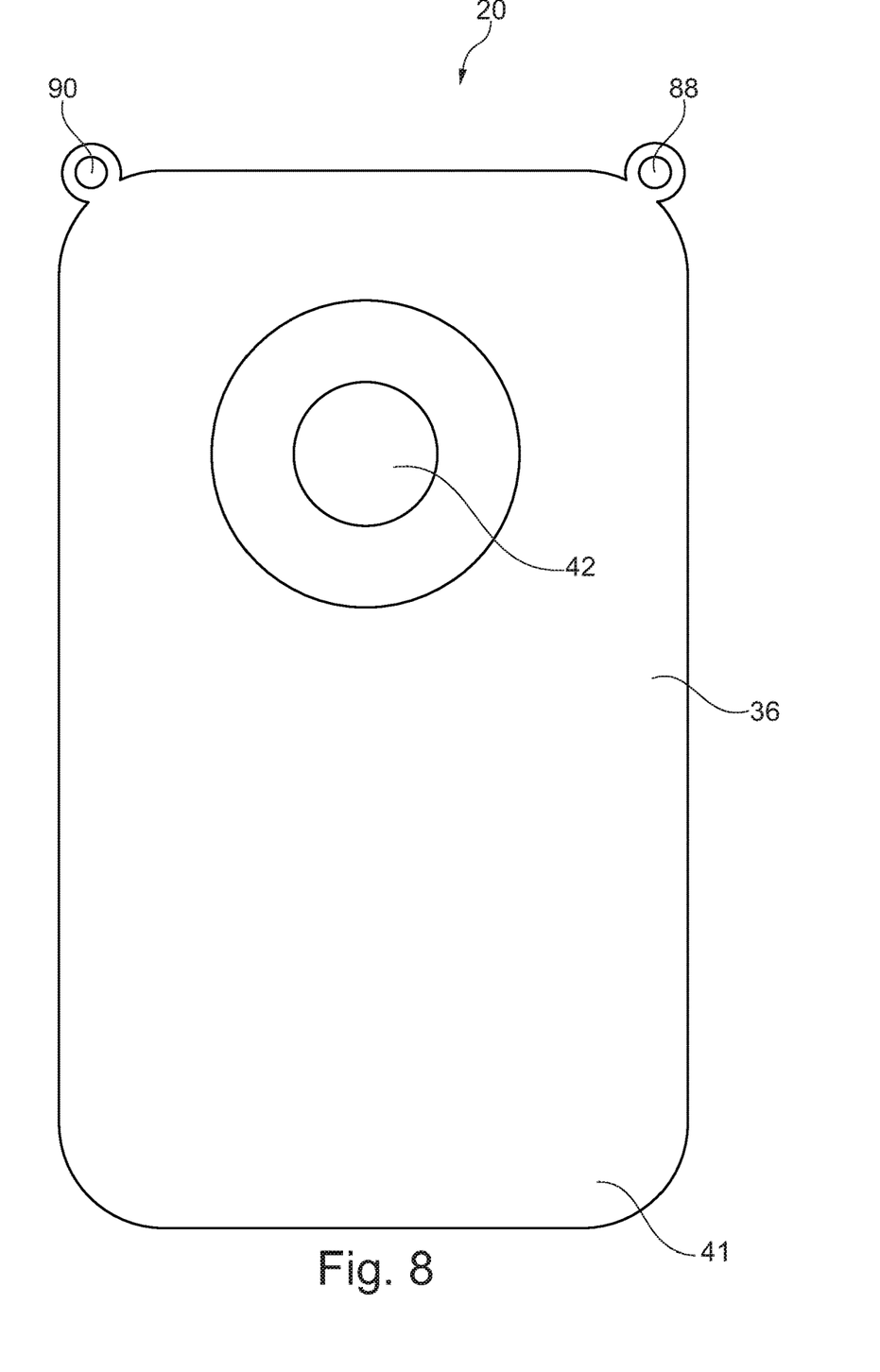
FIG. 8 is a view showing schematic details of a belt attachment connection according to one embodiment of an ostomy appliance.

FIG. 8 illustrates one embodiment wherein the collecting bag 36 comprises a first grommet 88 located laterally relative to a second grommet 90, the first and the second grommet 88, 90 placed on the collecting bag 36 relatively closer to a top portion 43 of the collecting bag 36 than to a bottom portion 41 of the collecting bag 36 and above the inlet opening 42. In the embodiment of FIG. 8, the collecting bag 36 is a closed collecting bag having no outlet at the lower portion 41. In embodiments, the grommets 88, 90 provide an alternative or additional means for carrying the weight of the collecting bag 36. In embodiments, the grommets 88, 90 are adapted to connect with mating grommets or loops on an ostomy belt (not shown).

In another aspect, the present disclosure relates to a sealing wafer for an ostomy appliance including a backing film having a distal side and a proximal side. An adhesive material is provided on the proximal side of the backing film and a first half of a coupling interface configured as a pipe section that is attached to the distal side of the backing film.

In another aspect, the present disclosure relates to a kit of parts including a sealing wafer, at least one collecting bag and optionally a set of instructions for use of the kit of parts. The sealing wafer includes a backing film having a distal side and a proximal side. The proximal side of the backing film is adapted to support an adhesive material. A second half of a coupling interface is configured as a second pipe section and is attached to the distal side of the backing film. The at least one collecting bag is adapted for collection of bodily waste fluids and includes a first half of a coupling interface attached to the collecting bag by a plastic tube. The first half of the coupling interface is configured as a first pipe section and is adapted to couple with the second pipe section of the second half of the coupling interface of the sealing wafer. The optional set of instructions for use of the kit of parts can be provided as a set of paper pages, a pamphlet, brochure and/or by electronic information means provided on any relevant type of data storage medium and/or by reference to a webpage containing the instructions, the reference to the webpage delivered as part of the kit of parts. In embodiments, the kit of parts further includes a packaging.

In embodiments of the kit of parts, the backing film of the sealing wafer comprises a silicone material adapted to be rinsed with water or a watery solution.

In embodiments, the kit of parts further comprises at least one unit of adhesive paste material adapted to be connected to the proximal side of the backing film. In an alternative embodiment, the kit of parts comprises an adhesive material disposed directly on the proximal surface of the sealing wafer.

In embodiments, the collecting bag of the kit of parts comprises a second adhesive located such as to surround the first half of the coupling interface.

In another aspect, the present disclosure relates to the use of the kit of parts disclosed herein for preparing an ostomy appliance for an ostomist.

In another aspect, the present disclosure relates to the use of a kit of parts disclosed herein for improving the skin condition of the peristomal skin surface of an ostomist.

In another aspect, the present disclosure relates to the use of an ostomy appliance as disclosed herein for improving the skin condition of the peristomal skin surface of an ostomist.

Embodiments of the present disclosure provide an ostomy appliance that offers improved handling and facilitates easier attachment to the peristomal skin surface for the user. Providing an ostomy appliance wherein the adhesive interface with the skin surface of the user is separated into a first adhesive zone close to the stoma (in the peristomal area) and a second adhesive zone surrounding the first adhesive zone is furthermore advantageous in that it allows the user better access and visibility to the peristomal area. In other words, it allows for the user to apply the ostomy appliance in a more optimized manner because he/she can easily access and better see the first adhesive zone when attaching the first adhesive around the stoma. The distal surface of the sealing wafer is exposed and accessible, for example to facilitate the attachment of the first adhesive of the sealing wafer. Only when the user is satisfied with the attachment to the skin of the first adhesive around the stoma does the user need to pay attention to attaching the second (outer) adhesive zone surrounding the sealing wafer. In support of this, embodiments include providing at least two separate release liners, one on the first adhesive and one on the second adhesive. In embodiments, more than one release liner on each of the adhesives can be applied and be advantageous.

Embodiments provide an ostomy appliance that reduces the likelihood that stomal output reaches the adhesive zone of the appliance located immediately around the user's stoma in use. Moreover, to the extent that some stomal output does enter underneath such adhesive zone and starts attacking the adhesive matrix, the capability of the ostomy appliance to maintain adhesion for carrying the weight of the appliance and of the accumulated output in the collecting bag is not affected.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

The invention claimed is:

1. An ostomy appliance, comprising:
    a sealing wafer having an outermost periphery, the sealing wafer defining a first proximal surface and a second distal surface, the first proximal surface provided with a first adhesive, the sealing wafer defining a stoma-receiving opening;
    a collecting bag having a proximal wall and a distal wall and an inlet opening in the proximal wall for receiving stomal output;
    the sealing wafer adapted to be connectible to the collecting bag; and
    a second adhesive provided on the proximal wall of the collecting bag around the inlet opening;
    wherein, in use of the ostomy appliance, the outermost periphery of the sealing wafer is adapted to be located radially closer to the stoma-receiving opening and the inlet opening than any portion of the second adhesive on the proximal wall of the collecting bag.

2. The ostomy appliance of claim 1, wherein the sealing wafer and the collecting bag are fixedly connected to each other.

3. The ostomy appliance of claim 1, wherein the sealing wafer and the collecting bag are detachably connected to each other.

4. The ostomy appliance of claim 1, wherein a first half of a coupling interface is provided on the proximal wall of the collecting bag and a second half of the coupling interface is attached to the second distal surface of the adhesive wafer.

5. The ostomy appliance of claim 4, wherein the first half of the coupling interface is connected to the proximal wall of the collecting bag by a plastic tube.

6. The ostomy appliance of claim 4, wherein the second half of the coupling interface is connected to the second distal surface of the adhesive wafer by a plastic tube.

7. The ostomy appliance of claim 1, wherein a first end of a plastic tube is attached to the second distal surface of the sealing wafer and a second end of the plastic tube is attached to the proximal wall of the collecting bag.

8. The ostomy appliance of claim 5, wherein the plastic tube comprises a plication allowing the plastic tube to be extended such that the sealing wafer is movable relative to the proximal wall of the collecting bag.

9. The ostomy appliance of claim 5, wherein the plastic tube is configured with a conical shape such that the plastic tube has a first, relatively larger diameter at the proximal wall of the collecting bag and a second, relatively lesser diameter at the sealing wafer.

10. The ostomy appliance of claim 6, wherein the plastic tube is connected to the second half of the coupling interface of the sealing wafer.

11. The ostomy appliance of claim 4, wherein the first half of the coupling interface comprises a first pipe section and the second half of the coupling interface comprises a second pipe section.

12. The ostomy appliance of claim 11, wherein an outer surface of the first pipe section and an outer surface of the second pipe section are a conical shape.

13. The ostomy appliance of claim 11, wherein an inner surface of the first pipe section and an inner surface of the second pipe section are a conical shape.

14. The ostomy appliance of claim 11, wherein all points on an outer surface of a major portion of the second pipe section are located with an equal distance to a centre axis through the second pipe section, such that the major portion of the outer surface forms the shape of a cylinder.

15. The ostomy appliance of claim 11, wherein all points on an inner surface of the first pipe section is provided having an equal distance to a centre axis through the first pipe section such that an inner lumen of the first pipe section forms the shape of a cylinder.

16. The ostomy appliance of claim 4, wherein the coupling interface is configured to provide a signal indicating in response to correct coupling of the coupling interface.

17. The ostomy appliance of claim 16, wherein the signal is a sound signal.

18. The ostomy appliance of claim 11, wherein the second pipe section has a longitudinal extent measured parallel to a centre axis through the second pipe section of 15-40 mm.

19. The ostomy appliance of claim 4, wherein the second half of the coupling interface comprises a collar.

20. The ostomy appliance of claim 19, wherein the collar comprises a neck portion.

21. The ostomy appliance of claim 17, wherein the sound signal is generated mechanically.

22. The ostomy appliance of claim 1, wherein the sealing wafer is connected to the proximal wall of the collecting bag by a plastic tube such that the second distal surface of the sealing wafer is movable parallel to the proximal wall of the collecting bag.

23. The ostomy appliance of claim 1, wherein the second adhesive is provided on the proximal wall of the collecting bag annularly around the inlet opening.

24. The ostomy appliance of claim 1, wherein the collecting bag comprises a first grommet located laterally relative to a second grommet, the first and the second grommet placed on the collecting bag relatively closer to a top portion of the collecting bag than to a bottom portion of the collecting bag and above the inlet opening.

25. The ostomy appliance of claim 1, wherein the second distal surface of the sealing wafer is configured to be accessible to the fingers of a user at least during application of the sealing wafer to peristomal skin.

26. The ostomy appliance of claim 1, wherein the second adhesive is provided directly in contact with the proximal wall of the collecting bag.

27. The ostomy appliance of claim 4, wherein the first half of the coupling interface is in direct attachment with the proximal wall of the collecting bag.

28. The ostomy appliance of claim 8, wherein the plastic tube comprises a plurality of plications that combine to form an accordion-like structure of the plastic tube between the second distal surface of the sealing wafer and the proximal wall of the collecting bag.

* * * * *

UNITED STATES PATENT AND TRADEMARK OFFICE
CERTIFICATE OF CORRECTION

| | | |
|---|---|---|
| PATENT NO. | : 11,219,547 B2 | |
| APPLICATION NO. | : 15/769742 | |
| DATED | : January 11, 2022 | |
| INVENTOR(S) | : Schertiger et al. | |

It is certified that error appears in the above-identified patent and that said Letters Patent is hereby corrected as shown below:

On the Title Page

Item (57), under "ABSTRACT", in Column 2, Line 10, delete "pipe sections (50)." and insert -- pipe sections (60, 62). --, therefor.

In the Specification

In Column 7, Line 26, delete "section pipe" and insert -- second pipe --, therefor.

In the Claims

In Column 12, Line 27, in Claim 8, delete "a plication" and insert -- application --, therefor.

In Column 14, Line 13, in Claim 28, delete "of plications" and insert -- of applications --, therefor.

Signed and Sealed this
Second Day of August, 2022

Katherine Kelly Vidal
*Director of the United States Patent and Trademark Office*